United States Patent [19]

Remy

[11] Patent Number: 4,605,660
[45] Date of Patent: Aug. 12, 1986

[54] INDENO[2,1-C]PYRIDINE COMPOUNDS, AND THEIR USE AS CALCIUM CHANNEL BLOCKERS

[75] Inventor: David C. Remy, North Wales, Pa.

[73] Assignee: Merck & Co., Inc., Rahway, N.J.

[21] Appl. No.: 740,617

[22] Filed: Jun. 3, 1985

[51] Int. Cl.$^4$ ................... A61K 31/395; C07D 221/16
[52] U.S. Cl. ....................................... 514/290; 546/111
[58] Field of Search ......................... 546/111; 514/290

[56] References Cited

U.S. PATENT DOCUMENTS

| | | | |
|---|---|---|---|
| 3,905,970 | 9/1975 | Bossert et al. | 546/290 |
| 3,923,818 | 12/1975 | Bossert et al. | 546/290 |
| 4,044,141 | 8/1977 | Bossert et al. | 546/290 |
| 4,237,137 | 12/1980 | Tacke et al. | 546/290 |
| 4,285,955 | 8/1981 | Wehinger et al. | 546/290 |

OTHER PUBLICATIONS

Weller et al., J. Org. Chem., 48, pp. 3061–3067 (1983).
Goldmann, Angew. Chem. Int. Ed. Edl., 20, pp. 779–780 (1981).

Primary Examiner—Henry R. Jiles
Assistant Examiner—J. Richter
Attorney, Agent, or Firm—Alice O. Robertson; Michael C. Sudol

[57] ABSTRACT

Indeno[2,1-c]pyridine compounds, particularly cyano substituted tetrahydroindeno[2,1-c]pyridine dicarboxylic acid ester compounds, their preparation and their use as calcium entry blockers are disclosed.

11 Claims, No Drawings

INDENO[2,1-C]PYRIDINE COMPOUNDS, AND THEIR USE AS CALCIUM CHANNEL BLOCKERS

DESCRIPTION OF THE INVENTION

The present invention is directed to cyano substituted indeno[2,1-c]pyridine dicarboxylic acid ester compounds, more specifically to 4a(R,S),9a(S,R)-dialkyl 1-cyano-1,3-dimethyl-2,4a,9,9a-tetrahydro-9H-indeno[2,1-c]pyridine-4,9a-dicarboxylate compounds represented by the formula:

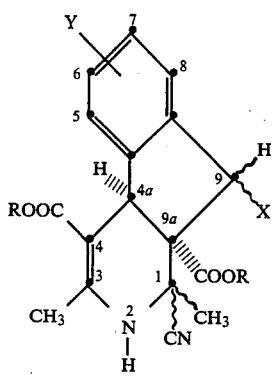

(I)

The numbering refers to positions for the substituents in the compound. In this and succeeding formulas, the ◢ and ⌇ bond designation for forward or above the plane and behind or below the plane are employed in a conventional manner, and the ⌇ bond designation is employed to designate that the bond may be above or below the plane of the molecule; X is hydroxy, chlorine, bromine or acyloxy, Y is hydrogen, nitro, halogen, loweralkyl, lower alkoxy or trifluoromethyl, and R is lower alkyl.

By "halogen" as herein employed is meant chlorine, bromine, fluorine or iodine. By "acyloxy" is meant a group resulting from esterification of the hydroxy group with a lower aliphatic acid. Representative acids from which the ester groups are derived may be represented by R'COOH where R' is from 1 to 6 carbon atoms and include acetic, hexanoic, pentanoic, butanoic, and propanoic acids. By "lower alkyl" is meant an alkyl group having from 1 to 6 carbon atoms, which may be straight chain or branched. Representative groups include methyl, isopropyl, tertiarybutyl, isoamyl, n-hexyl, 2,2-dimethylpropyl, ethyl, n-butyl and the like.

The compounds of the present invention are capable of existing in stereoisomeric forms. The hydrogen and the ester groups attached to the carbon atoms at the juncture of the tetrahydropyridine and the indene rings are both in the same direction relative to the "plane" of the molecule. The cyano group may enter in a manner to produce a substituted product in which the cyano group may be in the same plane as the hydrogen and carbalkoxy group or in the opposite plane. This may be seen in Formulas IIIA and IIIB.

The products of the present invention are crystalline solids, soluble in most nonpolar organic solvents. Pharmacological properties adaptable for therapeutic application are shown by the compounds of the present invention. The compounds have shown properties of inhibiting calcium induced contraction of tracheal smooth muscle or vascular tissue rendering them adaptable for therapeutic application as cardiovascular agents.

The compounds of the present invention may be prepared through reactions or a series of reactions in which certain of the compounds of the present invention are intermediates in the preparation of certain other compounds of the present invention. The starting material for the reaction is a dihydropyridine compound of the formula:

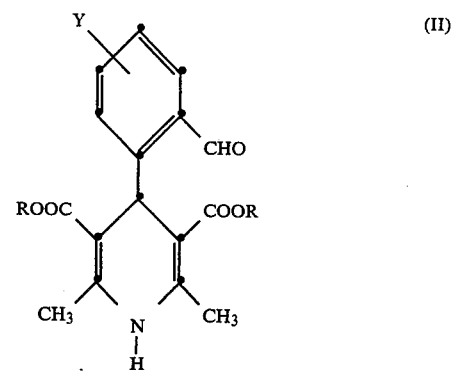

(II)

These compounds are generally known in the literature. They may be prepared by a method subsequently described.

When the products of the present invention are those in which X is hydroxy as seen in Formula III,

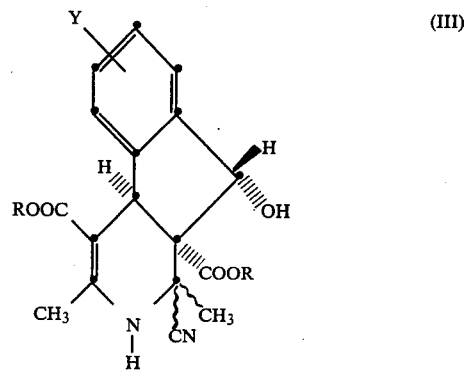

(III)

they may be prepared by reacting the dihydropyridine compound (II) with trialkylsilyl cyanide in the presence of a Lewis acid catalyst whereupon the cyanide group is introduced into the pyridine ring and cyclization takes place to obtain a silyl ether of III which when reacted with tetraalkyl ammonium fluoride is desilylated to obtain dialkyl 1-cyanotetrahydroindenopyridine compound (III) in the isomeric forms (IIIa) and (IIIb). One of the isomers (slow moving), separates as crystals from the reaction mixture and may be recovered by filtration. The other isomer (fast moving) may be thereafter recovered from the filtrate by appropriate crystallization procedures. The expressions "slow moving" and "fast moving" refer to relative rates of movement of the isomers when employing chromatographic system of separation on silica gel using a 70 percent ether in hexane solvent system.

The compounds in which the substituent at the 9 position is an acyloxy group, i.e., the hydroxy group is esterified, may be prepared by reacting Compound III with an acylating agent to obtain an acylated product Compound IV which may be IVA if the starting material is IIIA and IVB if the starting material is IIIB.

The compounds in which the substituent at the 9 position is halogen may be prepared by reacting Compound III with a halogen substituting agent such as sulfonyl halide. The reaction proceeds with inversion of the 9-position. Thus, from IIIA, the product is V; from IIIB, the product would be a epimer at the 9-position (not shown).

The sequence of reactions may be seen in the following flow diagram:

Suitable reagents for this are trialkylsilyl cyanides, preferably, trimethylsilyl cyanide. The Lewis acid is also used in catalytic amounts. Suitable Lewis acids include zinc iodide, zinc chloride, aluminum chloride, boron trifluoride, ferric chloride and the like. The reaction is carried out in an inert solvent. Preferred solvents are halohydrocarbon solvent such as methylene chloride, chloroform, ethylene chloride, carbon tetrachloride and the like, although other inert solvents such as aromatic hydrocarbon solvents, e.g. toluene, xylene and the like also may be employed.

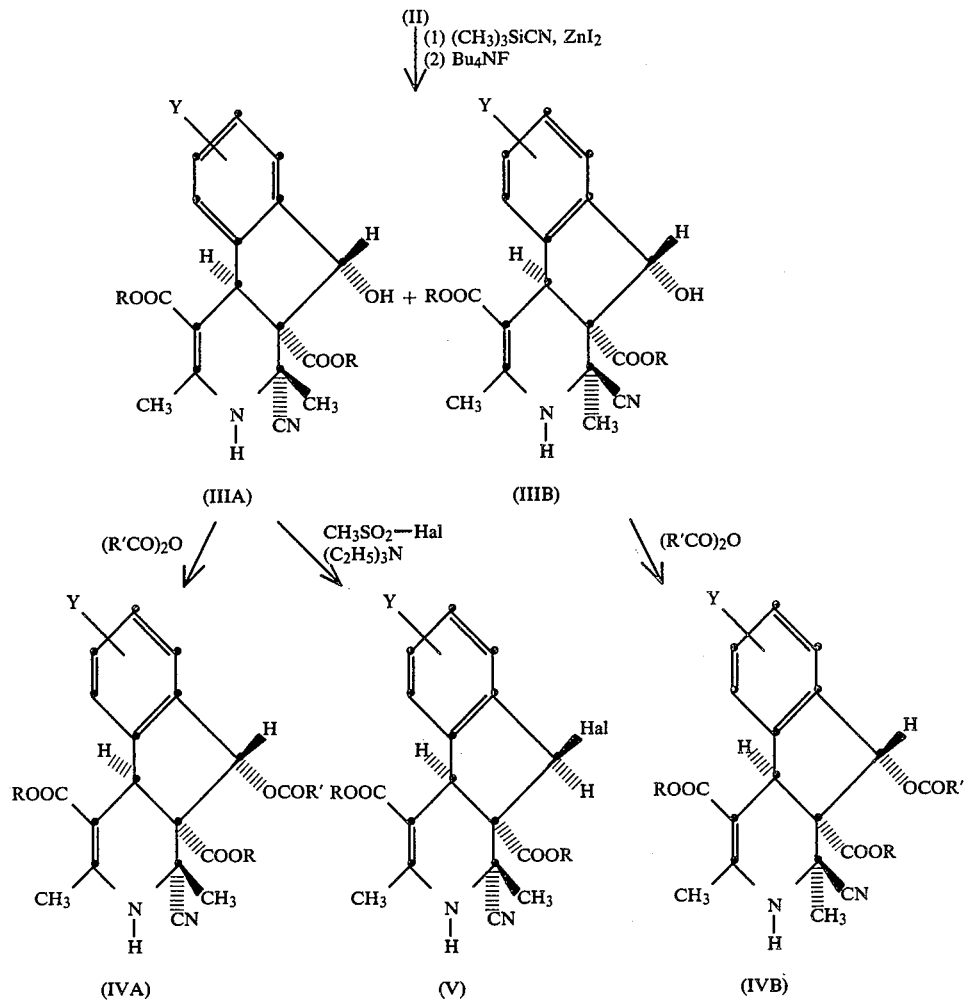

In the reaction for the preparation of (III), the dihydropyridine compound (II) is intimately contacted with trialkylsilyl cyanide and Lewis acid such as zinc iodide in an inert solvent for time sufficient to complete the reaction with the formation of an intermediate product containing a cyano group. The latter is recovered from the reaction mixture as residue by evaporating off the solvent, and then is dissolved in an inert solvent, preferably an ethereal solvent, and a solution for cleavage of the silyl ether bond is added thereto and the mixture allowed to stand at ambient temperature for time sufficient to complete the reaction with the formation of the hydroxyindenopyridine product of Formula (III) as a crystalline solid. The product may be recovered and purified by conventional procedures.

For the first step in this preparation of (III), the cyanide group supplying reagent is used in molar excess, preferably from about two to five-fold molar excess.

In carrying out the first step, the reactants are stirred together. Preferably, the Lewis acid is added to a stirred solution of the dihydropyridine compound (II) and trialkyl silyl cyanide in an inert solvent at ambient temperature. The reaction mixture then is stirred for time sufficient to complete the reaction. Usually stirring is carried out at least for several hours and conveniently is carried out overnight.

In the second step, the intermediate silyl ether product is cleaved to produce the desired Compound III (as IIIA or IIIB). Suitable agents for this reaction include tetraalkylammonium fluorides. Tetrabutyl ammonium fluoride is a preferred reagent. Solvents suitable for this step are the ethereal solvents generally employed for this type of reaction. Tetrahydrofuran is especially suitable. Other inert solvents such as diethyl ether, diisopropyl ether, dioxane and the like also may be employed.

In carrying out this step, a solution of the tetraalkylammonium fluoride in an inert solvent is added preferably with stirring at ambient temperature to the solution of the intermediate and the stirring continued until completion of the reaction with the formation of the desired indeno[2,1-c]pyridine compound (III) in the reaction mixture. Compound III is obtained in two steroisomeric forms. One of the isomers crystallizes first and may be recovered employing conventional procedures for isolation. The second isomer may be recovered from the mother liquor by conventional isolation and purification procedures. Thus, the mother liquor may be evaporated down, the residue purified by adsorption or crystallization, and recrystallized to the desired product.

The compounds represented by Formula (IV) may be prepared from the hydroxy compound, Compound III (IIIA or IIIB), in a conventional acylation reaction. The reaction proceeds with retention of configuration.

Acylating agent may be acid anhydride or acid halide and is employed in molar excess. The particular acylating agent will depend on the ester group desired.

A basic solvent is employed as reaction medium. Pyridine, commonly employed, is convenient although other tertiary amine bases are also suitable.

Generally, the temperature of addition is ambient but the reaction may be completed at elevated temperatures, generally in the range 70°-130° C. Refluxing temperature of the solvent is convenient.

In carrying out the reaction, the hydroxy compound and acid anhydride or chloride in an appropriate solvent may be heated together under reflux for time sufficient to complete the reaction with the formation of the desired ester product in the reaction mixture. The product then may be recovered by allowing the mixture to cool, diluting with water, extracting with water-immiscible organic solvent and recovering from the organic solution in a conventional manner.

The compounds represented by Formula (V) or its epimeric isomer may be prepared from the hydroxy compound, Formula IIIA or IIIB, by a displacement reaction employing a number of appropriate agents suitable for displacing hydroxyl with the appropriate halogen.

Suitable displacing agents for the reaction are alkyl sulfonyl halides although other displacing agents such as hydrogen halide with or without metal halide catalyst, phosphorus oxychloride, or even stronger agents such as, phosphorus trichloride, phosphorus pentachloride and the like may be employed.

The reaction is generally preferably carried out employing an alkyl sulfonyl halide in the presence of excess amine. Suitable amines include triethylamine, and similar tertiary amines.

The reaction is generally also carried out in a solvent. Halohydrocarbon solvents such as those enumerated for an earlier step are also suitable for this step.

In carrying out the reaction, alkyl sulfonyl halide (or other halogenating agent) and amine base are added with stirring to a cooled solution of (III) in an inert solvent and the resulting mixture stirred from 6-20 hours, conveniently overnight to obtain the desired product of Formula (V) or its stereoisomer at the 9 position. At the end of this time, water is added to the reaction mixture and the product recovered using conventional procedures.

The usefulness of the compounds of the present invention as calcium entry blockers may be demonstrated by the ability of the compounds to inhibit contraction of tracheal smooth muscle or of vascular tissue. The property may be observed in a test in which segments of vascular smooth muscle obtained from male Sprague-Dawley rats are suspended in physiological salt solution in a tissue bath instrumented for recording contractions. After the tissue has been equilibrated, washed in calcium-free physiological salt solution and then depolarized, 1.0 mM calcium chloride is re-added to induce contraction. After the contraction has reached a plateau, tissues are washed and a test compound or vehicle is added to determine the effect on a second contraction achieved by the above cyclic protocol. From measuring the initial contraction as well as the second contraction in the presence of the test compound, the extent of inhibition may be calculated. The results of these tests for representative compounds in the compositions of the present invention are seen in the following table.

TABLE

| Active Component | Percent Inhibition of Contraction of Rat Aorta |
| --- | --- |
| 4a(R,S),9a(S,R)-Diethyl 1-cyano-1,3-dimethyl-2,4a,9,9a-tetrahydro-9-hydroxy-9H—indeno[2,1-c]pyridine-4,9a-dicarboxylate (Compound IIIA-1*) | 84% at $10^{-5}$ $\underline{M}$ |
| 4a(R,S),9a(S,R)-Diethyl 1-cyano-1,3-dimethyl-2,4a,9,9a-tetrahydro-9-hydroxy-9H—indeno[2,1-c]pyridine-4,9a-dicarboxylate (Compound IIIB-1*) | 52% at $10^{-6}$ $\underline{M}$ |
| 4a(R,S),9a(S,R)-Diethyl 9-acetoxy-1-cyano-2,4a,9,9a-tetrahydro-1,3-dimethyl-9H—indeno[2,1-c]pyridine-4,9a-dicarboxylate (Compound IVA-1*) | 62% at $10^{-5}$ $\underline{M}$ |
| 4a(R,S),9a(S,R)-Diethyl 9-acetoxy-1-cyano-2,4a,9,9a-tetrahydro-1,3-dimethyl-9H—indeno[2,1-c]pyridine-4,9a-dicarboxylate (Compound IVB-1*) | 6% at $10^{-6}$ M |
| 4a(R,S),9a(S,R)-Diethyl 9-chloro-1-cyano-2,4a,9,9a-tetrahydro-1,3-dimethyl-9H—indeno[2,1-c]pyridine-4,9a-dicarboxylate (Compound V-1*) | 24% at $10^{-5}$ M |
| 4a(R,S),9a(S,R)-Dimethyl 1-cyano-9-hydroxy-7-methoxy-2,4a,9,9a-tetrahydro-1,3-dimethyl-9H—indeno[2,1-c]pyridine-4,9a-dicarboxylate hydrate (Compound IIIA-2**) | 4% at $10^{-6}$ M |
| 4a(R,S),9a(S,R)-Dimethyl 1-cyano-9-hydroxy-7-methoxy-2,4a,9,9a-tetrahydro-1,3-dimethyl-9H—indeno[2,1-c]pyridine-4,9a-dicarboxylate (Compound IIIB-2**) | 2% at $10^{-6}$ M |

*when R is CH$_3$CH$_2$—
**when R is CH$_3$—

For use in the chemotherapeutic treatment of cardiovascular diseases, an effective amount of the compounds of the present invention may be administered orally, parenterally, by inhalation, or by suppository, and in any suitable dosage form. For oral administration, the compounds may be offered in the form of tablets or capsules with suitable dispersants and carrier materials or dispersed in a liquid carrier for administration as solution or aqueous dispersion or emulsion; for parenteral administration, the compounds may be dispersed in an appropriate liquid carrier with or without dispersing agents depending on whether a solution, emulsion or other dispersion is intended; for aerosol administration the compound may be dispersed formulated with a suitable dispersant and propellant; and for use as suppository the compounds may be dispersed in a suitable carrier. Suitable carriers and dispersants are hereinafter described.

The ratio of the compound of the present invention to carrier varies with the particular compound, purpose and the mode of administration. The dosage level for the compounds may be varied from about 0.3 milligram to about 10.0 milligrams per kilogram of body weight per day. Daily doses in the range of 1 to 10 mg/kg are preferred. These doses are suitable for any of the utilities described herein.

The free base may be formulated with a pharmaceutical carrier or diluent.

To prepare the pharmaceutical compositions of this invention, the compound of Formula (I) as the active ingredient, is intimately admixed with a pharmaceutical carrier according to conventional pharmaceutical compounding techniques, which carrier may take a wide variety of forms depending on the form of preparation desired for administration, e.g., oral or parenteral.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques.

For parenterals, the carrier will usually comprise sterile water, although other ingredients may be included, for purposes such as, for example, for aiding solubility or for preservation. Injectable suspensions also may be prepared, in which case appropriate liquid carriers, suspending agents and the like may be employed.

The pharmaceutical compositions herein will contain, per dosage unit, e.g., tablet, capsule, powder, injection, teaspoonful and the like, from about 10 to about 500 mg of the active ingredient, preferably, from about 10 to about 250 mg.

The following examples illustrate the invention but are not to be construed as limiting:

(In the following examples at times, the compound is referred back to the generic structure. "Compound IIIA-1" would indicate a compound with a specific substituent for Y or R but otherwise represented by the structure of Compound IIIA.)

EXAMPLE I

4a(R,S),9a(S,R)-Diethyl 1-cyano-1,3-dimethyl-2,4a,9,9a-tetrahydro-9-hydroxy-9H-indeno[2,1-c]pyridine-4,9a-dicarboxylate (Compound IIIA-1) (Slow Isomer)

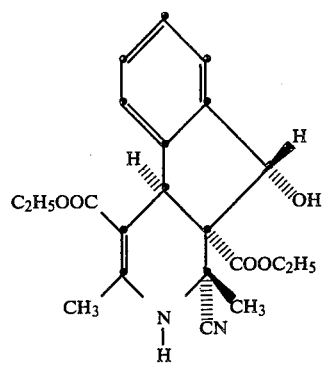

0.50 gram of zinc iodide was added to a stirred solution of 5.0 gram (0.014 mole) of diethyl 2,6-dimethyl-4-(o-formylphenyl)-1,4-dihydropyridine-3,5-dicarboxylate and 4.16 gram (0.042 mole) of trimethyl silyl cyanide in 75 milliliters of methylene chloride. The mixture was stirred at room temperature for 18 hours and thereafter the solvent evaporated to obtain a residue. The latter was dissolved in 200 milliliters of tetrahydrofuran and to the resulting solution was added 11.1 milliliters of a 1M solution of tetrabutylammonium fluoride in tetrahydrofuran and the mixture was stirred overnight. At the end of this period, the solvent was evaporated to obtain a residue which then was dissolved in ether, the ether solution washed with water, and then dried over magnesium sulfate. The drying agent was filtered off and some of the ether evaporated to obtain a more concentrated solution. The solution was scratched whereupon crystals of 4a(R,S),9a(S,R)-diethyl 1-cyano-1,3-dimethyl-2,4a,9,9a-tetrahydro-9-hydroxy-9H-indeno[2,1-c]pyridine-4,9a-dicarboxylate product formed. The product was recovered by filtration. The product after recrystallization from ether had a melting point of 173°–175° C. Elemental analyses of the product were as follows:

Calcd. for $C_{21}H_{24}N_2O_5$: C, 65.61; H, 6.29; N, 7.29 Found: C, 65.21; H, 6.22; N, 7.62.

EXAMPLE II

4a(R,S),9a(S,R)-Diethyl
1-cyano-1,3-dimethyl-2,4a,9,9a-tetrahydro-9-hydroxy-
9H-indeno[2,1-c]pyridine-4,9a-dicarboxylate
(Compound IIIB-1) (Fast Isomer)

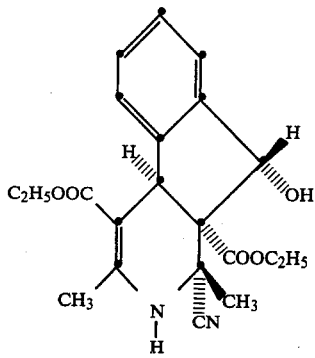

The filtrate obtained after the removal of the product of Example I was evaporated to dryness and the residue was chromatographed on silica gel using 70 percent ether in hexane. Examination of the chromatographic fractions showed a series of fractions having a homogeneous product which immediately preceded the position of that identifiable with that of the 173°–175° C. crystalline product of Example I. The fractions were pooled and the solvent evaporated to obtain a residue which after recrystallization from ether melted at 190°–192° C. The elemental analyses of the product were as follows:

Calcd. for $C_{21}H_{24}N_2O_5$: C, 65.61; H, 6.29; N, 7.29
Found: C, 65.27; H, 6.36; N, 7.38.

EXAMPLE III

4a(R,S),9a(S,R)-Diethyl
9-acetoxy-1-cyano-2,4a,9,9a-tetrahydro-1,3-dimethyl-
9H-indeno[2,1-c]pyridine-4,9a-dicarboxylate
(Compound IVA-1)

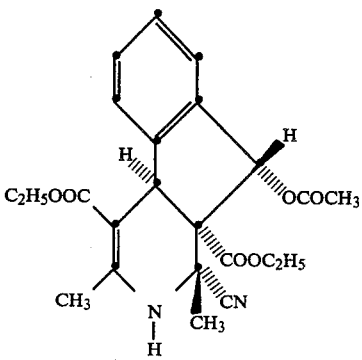

A solution of 0.158 gram (0.000411 mole) of the 4a(R,S),9a(S,R)-diethyl 1-cyano-1,3-dimethyl-2,4a,9,9a-tetrahydro-9-hydroxy-9H-indeno[2,1-c]-pyridine-4,9a-dicarboxyate of Example I and 10 drops of acetic anhydride in 4 milliliters of pyridine was stirred together under reflux for 30 minutes. At the end of this time, the solution was allowed to cool and the cooled solution diluted with 100 milliliters of water, and the diluted solution extracted with two 50 milliliter portions of ether. The combined extracts were washed with 2N hydrochloric acid, then with water and dried. The dried solution was concentrated whereupon the 4a(R,S),9a(S,R)-diethyl 9-acetoxy-1-cyano-2,4a,9,9a-tetrahydro-1,3-dimethyl-9H-indeno[2,1-c]pyridine-4,9a-dicarboxylate product precipitated as crystalline material. The melting point of the product was 155°–157° C. The elemental analyses of the product were as follows:

Calcd. for $C_{23}H_{26}N_2O_6$: C, 65.15; H, 6.15; N, 6.57.
Found: C, 64.77; H, 6.26; N, 6.72.

EXAMPLE IV

4a(R,S),9a(S,R)-Diethyl
9-acetoxy-1-cyano-2,4a,9,9a-tetrahydro-1,3-dimethyl-
9H-indeno[2,1-c]pyridine-4,9a-dicarboxylate
(Compound IVB-1)

A solution of 0.158 gram (0.000411 mole) of 4a(R,S),9a(S,R)-diethyl 1-cyano-1,3-dimethyl-2,4a,9,9a-tetrahydro-9-hydroxy-9H-indeno[2,1-c]-pyridine-4,9a-dicarboxylate obtained as described in Example II in 4 milliliters of pyridine and containing 20 crops of acetic anhydride was stirred under refluxed for about 30 minutes. Thereafter, the solution was allowed to cool and then diluted with 100 milliliters of water. The diluted solution was extracted with two 50 milliliter portions of ether. The ether extracts were combined and then washed successively with 2N hydrochloric acid and water, and then dried. The solvent was evaporated from the dried solution and the residue crystallized from ether to obtain a purified product, m.p. 178°–182° C. The product had the following elemental analyses:

Calc. for $C_{23}H_{26}N_2O_6$: C, 65.15; H, 6.15; N, 6.57.
Found: C, 65.04; H, 6.31; N, 6.41.

EXAMPLE V

4a(R,S),9a(S,R)-Diethyl
9-chloro-1-cyano-2,4a,9,9a-tetrahydro-1,3-dimethyl-
9H-indeno[2,1-c]pyridine-4,9a-dicarboxylate
(Compound V-1)

0.118 gram (0.00117 mole) of trethylamine and 0.10 gram (0.00086 mole) of methylsulfonyl chloride were added to a cold solution of 0.30 gram (0.00078 mole) of Compound IIIA-1 of Example I in 4 milliliters of methylene chloride and the resulting mixture stirred overnight at room temperature. At the end of this time, the solution was diluted with 200 milliliters of water and the diluted solution extracted with three 75 milliliter portions of ether. The ether solutions were combined and then washed and dried. The solvent was evaporated from the dried solution to obtain a residue which was purified by chromatography on silica gel developed in 25 percent hexane-75 percent ether. The product after elution from silica gel was crystallized from ether to obtain purified 4a(R,S),9a(S,R)-diethyl 9-chloro-1-cyano-2,4a,9,9a-tetrahydro-1,3-dimethyl-9H-indeno[2,1-c]pyridine-4,9a-decarboxylate product, m.p. 167°–168° C. The elemental analyses of the product were as follows:

Calcd. for $C_{21}H_{23}ClN_2O_4$: C, 62.60; H, 5.75; N, 6.96
Found: C, 62.50; H, 5.82; N, 6.53.

EXAMPLE VI

In operations carried out as described in Examples I and II, the following compounds were prepared:
(1) 4a(R,S),9a(S,R)-Dimethyl 1-cyano-9-hydroxy-7-methoxy-2,4a,9,9a-tetrahydro-1,3-dimethyl-9H-indeno[2,1-c]pyridine-4,9a-dicarboxylate hydrate (Compound IIIA-2) (Slow Isomer), m.p. 118° C.

Anal. Calcd. $C_{20}H_{22}N_2O_6H_2O$ C, 59.40; H, 5.98; N, 6.93; Found: C, 59.60; H, 5.52; N, 6.56.

(2) 4a(R,S),9a(S,R)-Dimethyl 1-cyano-9-hydroxy-7-methoxy-2,4a,9,9a-tetrahydro-1,3-dimethyl-9H-indeno[2,1-c]pyridine-4,9a-dicarboxylate (Compound IIIB-2) (Fast Isomer), m.p. 120°–121° C.

Anal. Calcd. $C_{20}H_{22}N_2O_6$ C, 62.16; H, 7.25; N, 5.74, Found: C, 62.40; H, 7.31; N, 5.79.

EXAMPLE VII

In operations carried out as described in Examples I and II, compounds having substituents indicated in the following tables may be prepared:

| Compound | R | Y |
|---|---|---|
| IIIA-3 | Et | 6-NO$_2$ |
| IIIB-3 | Et | 6-NO$_2$ |
| IIIA-4 | CH$_3$ | H |
| IIIB-4 | CH$_3$ | H |
| IIIA-5 | Et | 7-Cl |
| IIIB-5 | Et | 7-Cl |
| IIIA-6 | Et | 6-Br |
| IIIB-6 | Et | 6-Br |
| IIIA-7 | n-Bu | 6-CF$_3$ |
| IIIB-7 | n-Bu | 6-CF$_3$ |
| IIIA-8 | i-Pr | 5-F |
| IIIB-8 | i-Pr | 5-F |
| IIIA-9 | n-C$_6$H$_{13}$ | H |
| IIIB-9 | n-C$_6$H$_{13}$ | H |

EXAMPLE VIII

In operations carried out as described in Examples III and IV, compounds having substituents indicated in the following table may be prepared:

| Compound | R | Y | X |
|---|---|---|---|
| IVA-2 | Et | 6-NO$_2$ | OCOCH$_3$ |
| IVB-2 | Et | 6-NO$_2$ | OCOCH$_3$ |
| IVA-3 | CH$_3$ | H | OCOC$_2$H$_5$ |
| IVB-3 | CH$_3$ | H | OCOC$_2$H$_5$ |
| IVA-4 | Et | 7-Cl | OCO—n-C$_3$H$_7$ |
| IVB-4 | Et | 7-Cl | OCO—n-C$_3$H$_7$ |
| IVA-5 | Et | 6-Br | OCO—n-C$_5$H$_{11}$ |
| IVA-6 | n-Bu | 6-CF$_3$ | OCOCH$_3$ |
| IVA-7 | i-Pr | 5-F | OCOCH$_3$ |
| IVA-8 | n-C$_6$H$_{13}$ | H | OCOCH$_3$ |

EXAMPLE IX

In operations carried out as in a manner similar to that described in Example V, compounds having substituents indicated in the following table may be prepared:

| Compound | R | Y | X |
|---|---|---|---|
| VA-2 | Et | 6-NO$_2$ | Cl |
| VB-2 | Et | 6-NO$_2$ | Cl |
| VA-3 | CH$_3$ | H | Br |
| VB-3 | CH$_3$ | H | Br |
| VA-4 | Et | 7-Cl | Cl |
| VB-4 | Et | 7-Cl | Cl |

EXAMPLE X 10,000 hard gelatin capsules each containing as the active ingredient 25 milligrams of 4a(R,S),9a-(S,R)-diethyl 1-cyano-1,3-dimethyl-2,4a,9,9a-tetrahydro-9-hydroxy-9H-indeno[2,1-c]pyridine-4,9a-dicarboxylate (Compound IIIA-1) are prepared from the following formulation:

| | Grams |
|---|---|
| Active ingredient | 250 |
| Lactose | 750 |
| Starch | 250 |
| Talc | 250 |
| Calcium stearate | 10 |

A uniform mixture of the active and supplementary ingredients is prepared and filled into two-piece hard gelatin capsules. The capsules are suitable for oral administration to provide therapeutic relief for patients with cardiovascular disorders by alleviating cardiac arrhythmias and/or peripheral vasoconstriction.

EXAMPLE XI

Capsules are made by substituting for 4a(R,S)-,9a(S,R)-diethyl 1-cyano-1,3-dimethyl-2,4a,9,9a-tetrahydro-9-hydroxy-9H-indeno[2,1-c]pyridine in the formulation of Example X, one of the following:

(1) 4a(R,S),9a(S,R)-Diethyl 1-cyano-1,3-dimethyl-2,4a,9,9a-tetrahydro-9-hydroxy-9H-indeno[2,1-c]pyridine-4,9a-dicarboxylate (Compound IIIB-1);

(2) 4a(R,S),9a(S,R)-Diethyl 9-acetoxy-1-cyano-2,4a,9-,9a-tetrahydro-1,3-dimethyl-9H-indeno[2,1-c]-pyridine-4,9a-dicarboxylate (Compound IVA-1);

(3) 4a(R,S),9a(S,R)-Diethyl 9-acetoxy-1-cyano-2,4a,9-,9a-tetrahydro-1,3-dimethyl-9H-indeno[2,1-c]-pyridine-4,9a-dicarboxylate (Compound IVB-1);

(4) 4a(R,S),9a(S,R)-Diethyl 9-chloro-1-cyano-2,4a,9,9a-tetrahydro-1,3-dimethyl-9H-indeno[2,1-c]-pyridine-4,9a-dicarboxylate (Compound V-1).

EXAMPLE XII 5,000 compressed tablets, each containing as active ingredient 10 milligrams of 4a(R,S),9a(S,R)-diethyl 1-cyano-1,3-dimethyl-2,4a,9,9a-tetrahydro-9-hydroxy-9H-indeno[2,1-c]pyridine-4,9a-dicarboxylate (Compound IIIA-1) are prepared from the following formulation:

| | Grams |
|---|---|
| Active ingredient | 50 |
| Starch | 70 |
| Dibasic calcium phosphate hydrous | 500 |
| Calcium stearate | 2.5 |

The ingredients are finely powdered, mixed well, and then granulated with 10 percent starch paste. The granulation is dried and compressed into tablets using starch as a disintegrant and calcium stearate as lubricant.

PREPARATION OF STARTING MATERIAL

The 1,4-dihydropyridine diester starting materials of Formula II may be prepared through the following sequence of reactions:

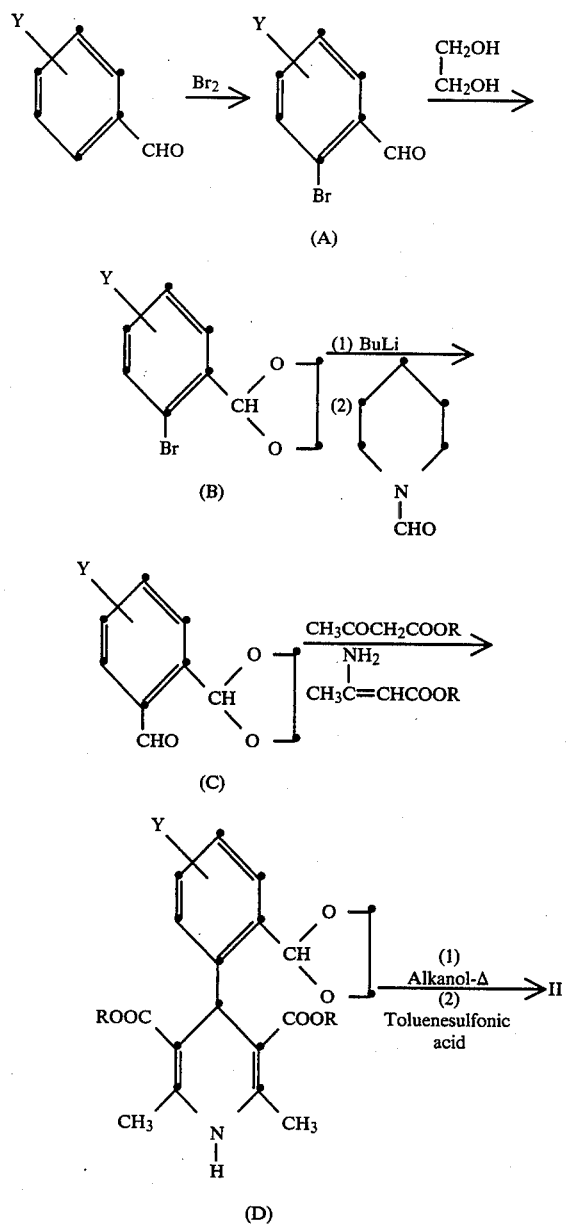

in an ethereal solvent such as tetrahydrofuran and thereafter, adding dropwise an ethereal solution of N-formylpiperidine to a still cooled to below −70° C. reaction mixture and the resulting mixture stirred first at the lower temperature and then while gradually allowing the temperature to rise to ambient temperature to obtain Compound C. The latter may be recovered from the mixture by acidifying the reaction mixture, extracting with ether, washing, drying, and concentrating under reduced pressure.

Compound C may be converted to the 1,4-dihydropyridine starting material of Formula II by heating together substantially equimolar proportions of Compound C, acetoacetic ester and alkyl β-aminocrotonate in a polar solvent such as an alkanol for time sufficient to complete the reaction with the formation of the diester product (D) and water by-product which may be codistilled with the alkanol. The dioxolanyl protecting group may then be removed by reaction with toluenesulfonic acid. The product (II) then may be recovered and purified employing conventional procedures.

When Y in the phenyl ring is a nitro group, the compounds are preferably prepared by an alternate method starting from x-nitro-1(3H)isobenzofuranone. (The "x" designates that the nitro group may be at any free position on the benzene ring.) In this alternate method, n-nitro-1(3H)isobenzofuranone is reacted with N-bromosuccinimide to first obtain a 3-bromo-x-nitro-1(3H)isobenzofuranone compound which when boiled with water forms a 3-hydroxy-x-nitro-1-(3H)isobenzofuranone compound. The latter is then treated with propane-1,3-dithiol and Lewis acid catalyst to obtain a 2-(1,3-dithian-2-yl)-x-nitrobenzoic acid compound which is first treated with a reducing agent such as borane to reduce the acid group to an alcohol group forming 2-(1,3-dithian-2-yl)-x-nitrobenzyl alcohol which when reacted with pyridinium chlorochromate forms a 2-(1,3-dithian-2-yl)-x-nitrobenzaldehyde compound. The benzaldehyde compound thus obtained is subjected to the Hantzch reaction, i.e., a reaction with alkyl acetoacetate and alkyl β-aminocrotonate to obtain a diester product similar to (D) in the preceeding sequence of reaction. The diester product on treatment with mercuric oxide and boron trifluoride etherate produces a dialkyl 4-(2-formyl-x-nitro)phenyl-2,6-dimethyl-1,4-dihydropyridine-3,5-dicarboxylate product corresponding to structure II when Y is nitro.

What is claimed is:

1. A compound having the structure:

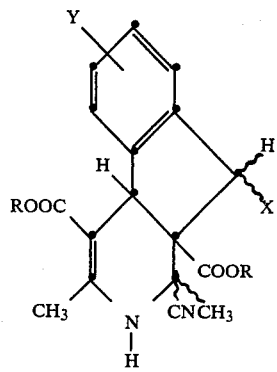

wherein the ⌇⌇⌇ bond designation indicates that the bond may be either above or below the plane of the molecule; X is hydroxy, halogen or acyloxy, Y is hydrogen, nitro, halogen or trifluoromethyl, and R is lower alkyl; wherein acyloxy is an ester group derived from R'COOH where R' is from 1 to 6 carbon atoms.

2. A compound according to claim 1 wherein X is hydroxy.

3. A compound according to claim 1 wherein X is halogen.

4. A compound according to claim 1 wherein X is acyloxy.

5. A compound according to claim 2 wherein Y is hydrogen and R is ethyl and the compound is named 4a(R,S),9a(S,R)-diethyl 1-cyano-1,3-dimethyl-2,4a,9,9a-tetrahydro-9-hydroxy-9H-indeno[2,1-c]-pyridine-4,9a-dicarboxylate.

6. A compound according to claim 3 wherein Y is hydrogen and R is ethyl and the compound is named 4a(R,S),9a(S,R)-diethyl 9-chloro-1-cyano-2,4a,9,9a-tetrahydro-1,3-dimethyl-9H-indeno[2,1-c]-pyridine-4,9a-dicarboxylate.

7. A compound according to claim 4 wherein Y is hydrogen and R is ethyl and the compound is named 4a(R,S),9a(S,R)-diethyl 9-acetoxy-1-cyano-2,4a,9,9a-tetrahydro-1,3-dimethyl-9H-indeno[2,1-c]-pyridine-4,9a-dicarboxylate.

8. A compound according to claim 2 wherein Y is methoxy and R is methyl and the compound is named 4a(R,S),9a(S,R)-dimethyl 1-cyano-9-hydroxy-7-methoxy-2,4a,9,9a-tetrahydro-1,3-dimethyl-9H-indeno[2,1-c]pyridine-4,9a-dicarboxylate hydrate.

9. A compound according to claim 2 wherein Y is methoxy and R is methyl and the compound is named 4a(R,S),9a(S,R)-dimethyl 1-cyano-9-hydroxy-7-methoxy-2,4a,9,9a-tetrahydro-1,3-dimethyl-9H-indeno[2,1-c]pyridine-4,9a-dicarboxylate.

10. A pharmaceutical composition useful in providing a calcium entry blocker in the chemotherapeutic treatment of cardiovascular diseases comprising a compound having the structure

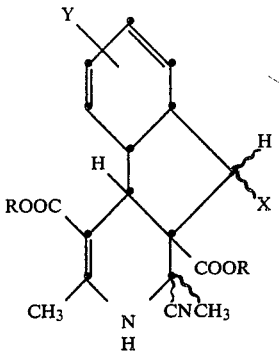

wherein the bond designation indicates that the bond may be above or below the plane of the ring; X is hydroxy, halogen or acyloxy, Y is hydrogen, nitro, halogen or trifluoromethyl, and R is lower alkyl and pharmaceutically acceptable salts thereof; wherein acyloxy is an ester group derived from an aliphatic acid R'COOH where R' is from 1 to 6 carbon atoms, and containing per dosage unit from about 10 to about 500 mg of the active ingredient.

11. A method for therapeutic treatment of cardiovascular disorders caused by calcium induced contraction of smooth muscle which comprises administering a therapeutically effective amount within the range of from about 0.3 milligram to about 10.0 milligrams per kilogram of body weight per day of a compound of claim 1.

* * * * *

UNITED STATES PATENT AND TRADEMARK OFFICE
CERTIFICATE OF CORRECTION

PATENT NO.   :   4,605,660
DATED        :   August 12, 1986
INVENTOR(S)  :   David C. Remy It is certified that error appears in the above—identified patent and that said Letters Patent is hereby corrected as shown below:

Column 16, line 21, "wherein the                                "

should be -- wherein the ~~~~ --

Signed and Sealed this

Twenty-third Day of December, 1986

*Attest:*

DONALD J. QUIGG

*Attesting Officer*     *Commissioner of Patents and Trademarks*